United States Patent [19]

Hayes et al.

[11] Patent Number: 4,518,578

[45] Date of Patent: May 21, 1985

[54] DENTIFRICE COMPOSITION CONTAINING VISUALLY CLEAR PIGMENT-COLORED STRIPE

[75] Inventors: Harry Hayes, Warrington; Kenneth Harvey, Wilmslow, both of England

[73] Assignee: Colgate-Palmolive Company, New York, N.Y.

[21] Appl. No.: 597,996

[22] Filed: Jun. 14, 1984

Related U.S. Application Data

[62] Division of Ser. No. 494,744, May 16, 1983, Pat. No. 4,456,585.

[51] Int. Cl.³ ............................................... A61K 9/16
[52] U.S. Cl. ........................................ 424/7.1; 424/49
[58] Field of Search ............................ 424/7.1, 49–58

[56] References Cited

U.S. PATENT DOCUMENTS

| | | | |
|---|---|---|---|
| 3,881,529 | 5/1975 | Mannara | 141/100 |
| 3,919,409 | 11/1975 | Perla et al. | 424/49 |
| 3,928,555 | 12/1975 | Gault | 424/49 |
| 3,928,559 | 12/1975 | Patino | 424/49 |
| 3,929,987 | 12/1975 | Colodney | 424/49 |
| 3,929,988 | 12/1975 | Barth | 424/49 |
| 3,935,306 | 1/1976 | Roberts et al. | 424/49 |
| 3,946,108 | 3/1976 | Tomlinson et al. | 424/49 |
| 3,952,782 | 4/1976 | Mannara | 141/100 |
| 3,955,942 | 5/1976 | Cordon | 424/49 |
| 3,957,964 | 5/1976 | Grimm | 424/49 |
| 3,957,968 | 5/1976 | Cordon | 424/49 |
| 3,980,767 | 9/1976 | Chown et al. | 424/49 |
| 4,002,732 | 1/1977 | Gault | 424/49 |
| 4,003,971 | 1/1977 | Mannara | 424/49 |
| 4,007,259 | 2/1977 | Patino et al. | 424/49 |
| 4,020,154 | 4/1977 | Perla et al. | 424/49 |
| 4,066,745 | 1/1978 | Tomlinson | 424/49 |
| 4,069,311 | 1/1978 | Mannara | 424/49 |
| 4,069,312 | 1/1978 | Mannara | 424/49 |
| 4,071,614 | 1/1978 | Grimm | 424/49 |
| 4,075,316 | 2/1978 | Cordon | 424/49 |
| 4,089,943 | 5/1978 | Roberts et al. | 424/49 |
| 4,098,435 | 7/1978 | Weyn | 222/94 |
| 4,122,976 | 10/1978 | Kenkare et al. | 222/94 |
| 4,211,341 | 7/1980 | Weyn | 424/49 X |
| 4,223,003 | 9/1980 | Scheller | 424/7.1 |
| 4,240,566 | 12/1980 | Bergman | 206/219 |
| 4,254,894 | 3/1981 | Fetters | 222/1 |
| 4,368,089 | 1/1983 | Smith | 424/49 |
| 4,376,762 | 3/1983 | Hauschild et al. | 424/49 |
| 4,376,763 | 3/1983 | Barth et al. | 424/49 |
| 4,444,746 | 4/1984 | Hayes et al. | 424/49 |
| 4,456,585 | 6/1984 | Hayes et al. | 424/49 |

*Primary Examiner*—Shep K. Rose
*Attorney, Agent, or Firm*—Robert L. Stone; Murray M. Grill; Herbert S. Sylvester

[57] ABSTRACT

A visually clear pigmented dentifrice in which a color-intensive conjugated pigment, such as a phthalocyanine is dispersed homogeneously throughout the clear dentifrice. The dentifrice is characterized as retaining color without substantial fading and with retention of clarity.

7 Claims, No Drawings

DENTIFRICE COMPOSITION CONTAINING VISUALLY CLEAR PIGMENT-COLORED STRIPE

This is a division of application Ser. No. 494,744 filed May 16, 1983, now U.S. Pat. No. 4,456,585, issued on June 26, 1984.

The present invention relates to visually clear dentifrices.

Visually clear dentifrices have been marketed in recent years in view of their desirable aesthetic aspect combined with their ability to provide desired hygenic and prophylactic effects to teeth and the oral cavity.

In visually clear dentifrices, it is necessary to select insoluble solid components with care since a close match between the refractive index of a solid component and the refractive index of the liquid vehicle is needed in order to provide clarity. For instance, a liquid vehicle mainly of glycerine and/or sorbitol with some water may be proportioned to have a refractive index of about 1.45 and a siliceous polishing material having a similar refractive index incorporated therein.

In order to increase their attractiveness, clear dentifrices have been dyed with water soluble dyes to make them red, yellow, orange, violet, blue, green or other colours. Indeed in British Pat. No. 1,289,323 a plurality of water-soluble dyes are used to make discreetly coloured portions of a clear dentifrice.

Hitherto, insoluble pigment materials have been generally avoided, since it would have been expected that the match of refractive indices needed for clarity between liquid and solid ingredients would be complicated by the presence of an undissolved, dispersed pigment. Indeed for this reason in British Application No. 81.35326, filed Nov. 24, 1981 (corresponding to U.S. Ser. No. 444,099 filed Nov. 24, 1982) to Harry Hayes and Kenneth Harvey, resort was had to lakes with colourless substrates in order to provide an insoluble non-fading colouring material which could be desirably used in visually clear dentifrices.

It is an advantage of the present invention that a colour-intensive insoluble pigment with a high pigment quantitive efficient electron system has been found to provide satisfactory colour to visually clear dentifrices without substantial fading and with sufficiently fine dispersion permitting retention of clarity.

Other advantages will be apparant from consideration of the following specification.

In accordance with certain of its aspects, this invention relates to a visually clear pigmented dentifrice comprising a liquid vehicle having a refractive index between about 1.36 and 1.47, up to about 10% by weight of a gelling agent, about 5–50% by weight of a polishing material having a refractive index similar to that of the said liquid vehicle, such that the said dentifrice is visually clear in appearance to the extent of being transparent or translucent when the said polishing material is dispersed in the said liquid vehicle and about 0.001–1.0% of a colour-intensive conjugated pigment dispersed homogeneously throughout said dentifrice.

The dentifrice of the present invention contains a liquid vehicle which generally comprises humectant and may include some water. The liquids are selected and if necessary, proportioned to have a refractive index between about 1.36 and 1.47. Refractive indices in this range provide a match to the refractive indices of dentifrice polishing agents such as sodium aluminosilicates (or silica containing combined alumina), described in British Pat. Nos. 1,348,492 and 1,347,650, silica xerogels, described in British Pat. Nos. 1,186,706 and 1,264,292, synthetic precipitated silica gel dentifrice polishing agents described in Published British Application No. 2,038,303A, such as is available from Grace G.m.b.H. of Norderstadt, Germany, as Syloblanc 81 and Syloblanc 82, insoluble potassium metaphosphate and water-soluble alkali metal phosphates described in British Pat. No. 1,424,034 and synthetic amorphous silica as described in U.S. Pat. Nos. 3,939,262 and 4,007,260.

The most commonly employed humectants for dentifrices are glycerine (refractive index of 1.47) and sorbitol (refractive index of 1.45 in 70% solution). Other humectants such as low molecular weight polyethylene glycols (e.g. having an average molecular weight of about 600) and propylene glycol may also be employed in a liquid vehicle having a proper refractive index.

Water may also form a portion of the liquid vehicle. Its refractive index is 1.33. When a polishing agent having a refractive index of about 1.44–1.47 is used, it may be necessary to limit the amount of free water to up to about 10% by weight of the dentifrice, e.g. about 3–5%; however, when polishing agents of lower refractive index, such as those described in British Pat. No. 1,424,034 and U.S. Pat. Nos. 3,939,262 and 4,007,260 are used, larger amounts of free water such as about 15% or more may be present. The expression "free water" refers to water which is not specifically associated with sorbitol or another dentifrice component. The liquid vehicle typically comprises at least about 20% by weight of the dentifrice, e.g. about 20–80%, preferably about 50–75%, e.g. about 50–60% or about 60–75%.

Polishing agents of the type which have refractive indices which can be closely matched with the refractive index of the liquid vehicle have been indicated above. In general, sodium aluminosilicate and silica xerogels having refractive indices in the range of about 1.44 to 1.47 are employed and the liquid vehicle is proportioned to have a refractive index similar to that of the polishing agent, typically within about 0.01 unit and preferably within about 0.005 unit or less. The polishing agent typically comprises about 5–50% by weight, preferably about 10–30% and most preferably about 15–25%, of the dentifrice.

In addition to the liquid vehicle, the dentifrice contains a solid vehicle portion of a gelling agent, possibly supplemented with a thickener, to provide gel character to the dentifrice. Typical gelling agents are natural or synthetic gum or gum-like materials, e.g. Irish moss, gum tragacanth, alkali metal carboxymethyl or carboxyethyl cellulose, hydroxyethyl cellulose, xanthan, polyvinyl pyrrolidone, starch, water-soluble hydrophilic colloidal carboxyvinyl polymers such as those sold under the trade names of Carbopol 934 and Carbopol 940 (CARBOPOL is a Trade Mark) and synthetic inorganic silicated clays such as those sold under the trade names Laponite CP and Laponite SP (LAPONITE is a Trade Mark). These grades of Laponite have the formula:

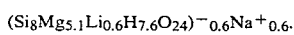

$$(Si_8Mg_{5.1}Li_{0.6}H_{7.6}O_{24})^-{}_{0.6}Na^+{}_{0.6}.$$

The solid portion of the vehicle is typically present in an amount up to 10% by weight of the dentifrice, preferably in the range from 0.1–5% by weight, typically about 0.1–2.0% or about 0.2–1%. When employed, such grades of Laponite are preferably used in amounts in the range of from 1 to 5% by weight.

Synthetic finely divided silicas such as those sold under the trade names Cab-O-Sil M-5, Syloid 24, Syloid 266, Aerosil D200 and Zeosyl 200 and mixtures thereof may also be employed in amounts of from 0.5 to 20% by weight, typically about 1–5% or 5–10%, to promote thickening or gelling and to improve the clarity of the dentifrice.

The pigment employed in the present invention is colour-intensive and is typically characterised by a conjugated cyclic structure with a high quantum efficient electron system. The high colour intensity is important since the total amount of pigment should be kept low, for instance, not more than about 1% by weight, in order to permit retention of dentifrice clarity. The colour-intensive pigments are best illustrated by the phthalocyanines.

Phthalocyanines are insoluble coloured organometallic compounds containing four symetrically arranged isoindole rings connected in a 16-membered ring linkage with alternate carbon and nitrogen atoms. Most phthalocyanines contain a central, co-ordinated metal ion, e.g. copper, nickel and cobalt. Also, there may be no metal ion at all. Copper phthalocyanines are illustrative of phthalocyanines and have the basic structure:

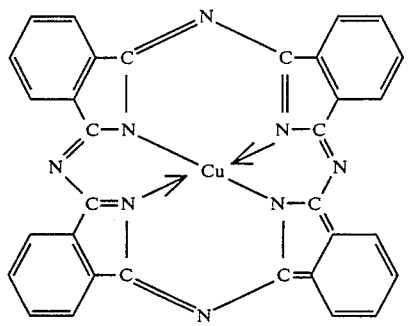

They provide colour-intense blue to green pigments which do not fade or substantially detract from clarity when homogeneously dispersed in clear dentifrices when present in amount of about 0.001–1% by weight, typically about 0.011–0.400%, preferably about 0.015–0.04% in a visually clear dentifrice. Such dentifrice may be a transparent or translucent gel or a stripe within a contrasting dentifrice or a surface stripe on a contrasting dentifrice.

When the dentifrice is entirely a transparent or translucent gel these pigments provide sufficient and appropriate colouration at surprisingly low concentrations which do not need to exceed 0.025% and thus ranges of 0.001 or 0.005 to 0.010 or 0.020% are preferred for such single colour unstriped gels.

When the coloured gel constitutes a stripe (and thus a minor proportion) in a white or constrasting striped toothpaste higher concentrations are found to be needed to give the best visual impact and thus for such toothpaste concentrations in the range 0.03 to 1% e.g. 0.1 to 0.5 or 0.2 to 0.4% are preferred.

It is noteworthy that in striped dentifrices the pigmented stripe portion does not leach colour into the contrasting portion as may happen when water-soluble dye is employed.

Phthalocyanine pigments have generally been employed in industry in view of their ability to provide intense colour. In the present invention copper phthalocyanines are highly desirable while other non-metal and metal phthalocyanines also provide sufficient colour intensity for use. It is understood that conjugated pigments other than phthalocyanines which provide equivalent colour-intensity may be employed such as Pigment Red 38 and Pigment Red 39. Pigments which are not colour-intensive would require too high level of presence in a dentifrice to permit retention of clarity. Such a pigment, which is not colour intensive, is the mineral cobalt aluminium spinal, $CoAl_2O_4$. On the other hand colour-intensive inorganic mineral pigments such as titanium dioxide do not permit retention of clarity.

The following pigments are illustrative phthalocyanine-type pigments:

| Pigment Name | Co-ordinated Ion | 1981 Colour Index No. | Colour |
| --- | --- | --- | --- |
| Pigment Blue 15 | Cu | 74160 | Bright Blue |
| Ingrain Blue 1 | Cu | 74240 | Bright Greenish-Blue |
| Pigment Blue 15 | Cu | 74250 | Bright Blue |
| Pigment Green 37 | Cu | 74255 | Bluish Green |
| Pigment Green 7 | Cu | 74260 | Bright Green |
| Pigment Blue 16 | (None) | 74110 | Bright Blue |
| Ingrain Blue 14 | Ni | 74160:1 | Greenish Blue |
| Ingrain Blue 5 | Co | 74160:2 | Blue |

C.I. 74160 is copper phthalocyanine; C.I. 74240 contains an onium group on each phenyl moiety; C.I. 74250 contains one chloro substituent; C.I. 74255 contains eight chloro substituents distributed evenly on the phenyl moieties; C.I. 74260 contains fifteen or sixteen chloro substituents distributed on the phenyl moieties; C.I. 74110 is phthalocyanine; C.I. 74160:1 is obtained from nickel polyisoindoline (C.I. 74161:1); C.I. 76160:2 is obtained from cobalt polyisoindoline (C.I. 74161:2). The preferred phthalocyanines contain copper ion, particularly Pigment Blue 15-C.I. 74160 and Pigment Green 7-C.I. 74260, available from D. F. Anstead, P.L.C., Billericay, Essex, England as 11918 Blue and 13956 Green, respectively.

The quality or depth of the colour intensity may be further modified, if desired, particularly when the pigment colour is not blue or green (e.g. when it is red), by including a water-soluble dye such as:

| PATENT DYESTUFF | 1971 COLOUR INDEX NUMBER |
| --- | --- |
| Ponceau 4R (red) | 16255 |
| Carmoisine (red) | 14720 |
| Amaranth (red) | 16185 |
| Erythrosine (pink) | 45430 |
| Red 2G (red) | 18050 |
| Tartrazine (yellow) | 19140 |
| Yellow 2G (yellow) | 18965 |
| Sunset Yellow (orange) | 15985 |
| Quinoline Yellow (yellow) | 47005 |
| D & C Red No. 19 | 45170 |
| D & C Red No. 21 | 45380 |
| D & C Red No. 27 | 45410 |
| D & C Orange No. 5 | 45370 |

Typically about 3–20 times as much pigment is used over the amount of such separate water-soluble dye depending largely on the particular surface area of blue pigments and the extent of the quantum efficiency of the electron system.

In accordance with a feature of this invention, the visually clear pigmented dentifrice may be present together with a visually clear non-coloured dentifrice or a visually clear dentifrice coloured by a pigment, lake or water-soluble dye of different, e.g. contrasting, colour or an opacified or opaque dentifrice. When this is the case, one portion of the dentifrice is present as a surface stripe of stripes on the other or as a stripe or stripes within the body of the other. In such striped dentifrices, the portions are generally similar in formulation except for colour.

Organic surface-active agents may be used in the compositions of the present invention to achieve increased prophylactic action, assist in achieving thorough and complete dispersion of the compositions of the present invention throughout the oral cavity, and render the compositions of the present invention more cosmetically acceptable. The organic surface-active material may be anionic, nonionic, ampholytic, or cationic in nature, and it is preferred to employ as the surface-active agent a detersive material which imparts to the composition detersive and foaming properties. Suitable types of such detergents include water-soluble salts of higher fatty acid monoglyceride monosulphates, such as the sodium salt of the monosulphated monoglyceride of hydrogenated coconut oil fatty higher alkyl sulphates, such as sodium lauryl sulphates, sodium $C_{12-18}$ alkyl sulphate, alkyl aryl sulphonates, such as sodium dodecyl benzene sulphonate, olefin sulphonates, such as sodium olefin sulphonate in which the olefin group contains 12–21 carbon atoms, higher alkyl sulphoacetates, higher fatty acid esters of 1,2-dihydroxy propane sulphonates, and the substantially saturated higher aliphatic acyl amides of lower aliphatic amino carboxylic acid compounds, such as those having 12–16 carbons in the fatty acid alkyl or acyl radicals. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of these compounds. The use of these sarcosine compounds in dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of sorbitan monostearate with approximately 20 moles of ethylene oxide, condensates of ethylene oxide with propylene oxide ("Pluronics") and amphoteric agents such as long chain (alkyl) amido-alkylene-alkylated amine derivatives, which are available under the trademark "Miranol" such as Miranol $C_2M$. Cationic surface active germicides and antibacterial compounds such as diisobutyl-phenoxyethyoxyethyl dimethyl benzyl ammonium chloride, benzyl dimethyl stearyl ammonium chloride, tertiary amines having one fatty alkyl group (of from 12–18 carbon atoms) and two (poly) oxyethylene groups attached to the nitrogen (typically containing a total of from 2 to 50 ethanoxy groups per molecule) and salts thereof with acids, and compounds of the structure

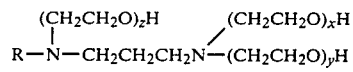

where R represents a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the oral preparation of the present invention.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, perillartine and sacharine. Suitably, flavour and sweetening agents may together comprise from about 0.01 to 5% or more of the composition of the present invention. Chloroform may also be used.

The compositions of the present invention may also contain a fluorine-containing compound having a beneficial effect on the care and hygiene of the oral cavity, e.g. diminution of enamel solubility in acid and protection of the teeth against decay which do not substantially detract from the clarity of the dentifrice. Examples thereof include sodium fluoride, potassium fluoride and complex fluorides, particularly sodium monofluorophosphate. These materials, which dissociate or release fluorine-containing ions, suitably may be present in an effective but non-toxic amount, usually within the range of about 0.01 to 1% by weight of the water-soluble fluorine content thereof. Sodium fluoride and sodium monofluorophosphate are particularly preferred as well as mixtures thereof.

Various other materials may be incorporated in the oral preparations of this invention. Examples thereof are colouring or whitening agents or dyestuffs, preservatives, silicones, chlorophyll compounds, ammoniated materials such as urea, diammoniumphosphate and mixtures thereof, and other constituents. The adjuvants are incorporated in the compositions of the present invention in amounts which do not substantially adversely affect the properties and characteristics desired and are selected and used in proper amounts depending upon the particular type of preparation involved.

Antibacterial agents may also be employed in the oral preparations of the present invention in an amount of about 0.01–5% by weight. Typical antibacterial agents include:

$N^1$-(4-chlorobenzyl)-$N^5$-(2,4-dichlorobenzyl biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1,6-bis(2-ethylhexylbiguanido)hexane;
1-(lauryldimethylammonium)-8-(p-chlorobenzyldimethylammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydro pyrimidine;
and their non-toxic acid addition salts.

In the manufacture of dentifrices, it is conventional to remove entrained air from the product by deaeration under vacuum typically at a late stage in the manufacture. If desired the dispersed, immobile air bubbles desirably can be permitted to remain as they can enhance the appearance of the dentifrice. Furthermore, air can be at least partially removed and reintroduced as substantially globular or spheroidal bubbles of say about 0.1–8 mm, preferably about 0.5–5 mm in size, well distributed in the gel at an average of at least one per cubic centimeter. Such air bubbles may be placed in the gel by stirring it while introducing air. Instead of air, bubbles of another gas, such as nitrogen or carbon dioxide, can be introduced in non-toxic quantity. In particular, carbon dioxide can provide an effervescent character to the dentifrice.

In the event it is desired to have a minimum amount of air in the dentifrice of the present invention, the "Unimix" apparatus described in "Process Engineering" Sept. 11, 1970, pages 81–85, is particularly efficacious for this purpose. In this apparatus a mixing tool can be rotated in clockwise or counterclockwise manner, and the action of the mixing tool is followed by the action of a scraper blade to ensure that the working surface of the apparatus is scraped clean. Preferably, a plastic such as polytetrafluoroethylene is used as the scraper since it is compatible with the various ingredients of the dentifrice. The positioning of the mixing tool and the scraper from a raised central column in the apparatus and the further presence of a hydraulically operated vacuum tight lid permits but little air to enter the formulation during processing. Thus, gelling agent and a portion of liquid including water and/or humectant can be efficiently blended in the Unimix apparatus. Then the remaining liquid can be separately blended with the polishing agent and additional components (except for post-added components, such as flavouring oil) in the Unimix, and then the two dispersions blended together in the Unimix apparatus. If desired, the small amount of air can be largely removed under the depressurized conditions in the apparatus. The apparatus can be used to blend ingredients at room temperature as well as at higher temperatures.

Furthermore, if desired, visible particles of dyes, pearlescent flakes or particles of insoluble salts of antibacterial agents such as the monofluorophosphate salt or the disarcosinate salt of 1,6-di-p-chlorophenylbiguanidohexane, as well as other particles, can be distributed in the dentifrice.

The dentifrices should have a pH practicable for use. A slightly acid to slightly alkaline pH is preferred. The dentifrices may be packaged in lined or unlined aluminium tubes, lined lead tubes, plastic tubes or aerosol or pump dispensers as well as tubes or dispensers adapted for striped dentifrices.

The invention may be put into practice in various ways and a number of specific embodiments will be described to illustrate the invention with reference to the accompanying Examples. All amounts are by weight unless otherwise indicated.

EXAMPLES 1 AND 2

Visually clear dentifrices are prepared and deaerated. The dentifrices have the following compositions:

|  | PARTS | |
|---|---|---|
|  | 1 | 2 |
| Glycerine | 25.000 | 25.000 |
| Sorbitol (70% aqueous solution | 48.980 | 48.980 |
| (Actual sorbitol) | 34.986 | 34.986 |
| Sodium saccharine | 0.200 | 0.200 |
| Sodium carboxymethyl cellulose | 0.260 | 0.260 |
| Pigment Green 7 C.I. 74260 (Anstead's 13956) | 0.020 | — |
| Pigment Blue 15 C.I. 74160 (Anstead's 11918) | — | 0.020 |
| Sodium monofluorophosphate | 0.760 | 0.760 |
| Sodium fluoride | 0.100 | 0.100 |
| Zeo 49 (ex Huber) Sodium aluminosilicate (silica with combined alumina) | 17.000 | 17.000 |
| Zeosyl 200 (silica thickener) | 7.000 | 7.000 |
| Sodium $C_{12-18}$ alkenyl sulphate | 1.500 | 1.500 |
| Flavour | 1.100 | 1.072 |
| Water | 2.936 | 4.415 |
| (Total water) | 16.930 | 18.409 |

The green and blue colours of the visually clear dentifrices remain intense and stable upon storage and the dentifrices remain visually clear.

The visually clear dentifrices of each of Examples 1 and 2 are varied by changing the amount of pigment to 0.010 and 0.025 parts respectively, with corresponding adjustments of the amounts of Sorbitol (70%).

EXAMPLE 3

The following colour-contrasting dentifrice portions are placed in a dentifrice dispenser to permit formation of a deep striped dentifrice upon extrusion, which deep striped dentifrice comprises 70% of white portion A and 30% of blue portion B.

|  | PARTS | |
|---|---|---|
|  | A(WHITE) | B(BLUE) |
| Glycerine | 25.000 | 25.000 |
| Sorbitol (70%) | 40.114 | 39.604 |
| Sodium saccharine | 0.170 | 0.170 |
| Sodium carboxymethyl cellulose | 0.260 | 0.260 |
| Polyethylene glycol 600 | 3.000 | 3.000 |
| Sodium monofluorophosphate | 0.820 | 0.820 |
| Titanium dioxide | 1.000 | — |
| Pigment Blue 15 | — | 0.030 |
| Pigment Green 7 | — | 0.001 |
| Tixosil 53 (ex Rhone-Poulenc) Sodium Aluminosilicate (silica with combined alumina) | 17.000 | 17.000 |
| Zeosyl 200 (silica thickener) | 7.100 | 7.100 |
| Sodium lauryl sulphate | 1.500 | 1.500 |
| Flavour | 1.100 | 1.100 |
| Water | 2.936 | 4.415 |

Upon extrusion intense and stable stripes of blue portion B are present within portion A.

EXAMPLE 4

The following colour-constrasting dentifrice portions are placed in a dentifrice dispenser to permit extrusion of a surface striped dentifrice which surface striped dentifrice comprises 98% of white portion A and 2% of green portion B.

|  | PARTS | |
| --- | --- | --- |
|  | A(WHITE) | B(GREEN) |
| Glycerine | 25.000 | 25.000 |
| Sorbitol (70%) | 40.142 | 39.142 |
| Sodium saccharine | 0.170 | 0.170 |
| Sodium carboxymethyl cellulose | 0.260 | 0.260 |
| Polyethylene Glycol 600 | 3.000 | 3.000 |
| Sodium monofluorophosphate | 0.820 | 0.820 |
| Titanium dioxide | 1.000 | — |
| Pigment Green 7 | — | 0.300 |
| Tixosil 53 | 17.000 | 17.000 |
| Zeosyl 200 | 7.100 | 7.100 |
| Sodium lauryl sulphate | 1.500 | 1.500 |
| Flavour | 1.072 | 1.072 |
| Water | 2.936 | 4.636 |

Upon extrusion intense and stable stripes of green portion B are present on the surface of white portion A.

Although this invention has been illustrated with reference to specific examples, it will be apparent to one skilled in the art that various modifications may be made thereto which fall within its scope.

We claim:

1. A dentifrice comprising a visually clear coloured dentifrice stripe together with a dentifrice which is clear and non-coloured, clear and of different colour or opaque, said coloured dentifrice stripe being coloured without requiring water-soluble dyes and comprising a liquid vehicle having a refractive index between about 1.36 and 1.47, up to about 10% by weight of a gelling agent, about 5–50% by weight of a polishing material having a refractive index similar to that of the said liquid vehicle, such that the said dentifrice stripe is visually clear in appearance to the extent of being transparent or translucent when the said polishing material is dispersed in the said liquid vehicle and about 0.001%–1% by weight of a colour-intensive insoluble conjugated pigment dispersed homogeneously without dissolution throughout said dentifrice stripe with sufficiently fine dispersion permitting retention of clarity, said dentifrice retaining colour imparted by said pigment without substantial fading and with retention of clarity.

2. A dentifrice as claimed in claim 1 in which said pigment is a phthalocyanine.

3. A dentifrice as claimed in claim 2 in which said phthalocyanine pigment contains a co-ordinated ion of copper, nickel or cobalt or no co-ordinated ion.

4. A dentifrice as claimed in claim 3 in which said phthalocyanine is a copper phthalocyanine.

5. A dentifrice as claimed in claim 4 in which the said copper phthalocyanine pigment is present in amount of about 0.01%–0.3% by weight.

6. A dentifrice as claimed in claim 5 in which the said copper phthalocyanine pigment is Pigment Blue 15-Colour Index 74160.

7. A dentifrice as claimed in claim 5 in which the said copper phthalocyanine pigment is Pigment Green 7-Colour Index 74260.

* * * * *